(12) United States Patent
Kato et al.

(10) Patent No.: US 12,109,062 B2
(45) Date of Patent: Oct. 8, 2024

(54) X-RAY DETECTOR AND MEDICAL IMAGE DIAGNOSTIC APPARATUS

(71) Applicant: CANON MEDICAL SYSTEMS CORPORATION, Otawara (JP)

(72) Inventors: Tooru Kato, Nasushiobara (JP); Hiroaki Miyazaki, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 267 days.

(21) Appl. No.: 17/178,758

(22) Filed: Feb. 18, 2021

(65) Prior Publication Data
US 2021/0251594 A1 Aug. 19, 2021

(30) Foreign Application Priority Data
Feb. 19, 2020 (JP) ................................ 2020-026346

(51) Int. Cl.
| | |
|---|---|
| G01T 1/17 | (2006.01) |
| A61B 6/00 | (2006.01) |
| A61B 6/03 | (2006.01) |
| A61B 6/42 | (2024.01) |

(52) U.S. Cl.
CPC ............... *A61B 6/54* (2013.01); *A61B 6/035* (2013.01); *A61B 6/4208* (2013.01); *A61B 6/4266* (2013.01); *G01T 1/17* (2013.01); *A61B 6/4275* (2013.01)

(58) Field of Classification Search
CPC ........... G01T 1/17; G01T 1/243; A61B 6/032; A61B 6/035; A61B 6/4208; A61B 6/4241; A61B 6/4266; A61B 6/4275; A61B 6/54; A61B 6/56
See application file for complete search history.

(56) References Cited

U.S. PATENT DOCUMENTS

2011/0075810 A1* 3/2011 Sendai .................. G21K 1/10
378/62
2012/0163543 A1* 6/2012 Fuse ..................... A61B 6/542
378/102

(Continued)

FOREIGN PATENT DOCUMENTS

| JP | 6-333696 A | 2/1994 |
|---|---|---|
| JP | 7-163044 A | 6/1995 |

*Primary Examiner* — Keith M Raymond
*Assistant Examiner* — Milton Truong
(74) *Attorney, Agent, or Firm* — Oblon, McClelland, Maier & Neustadt, L.L.P.

(57) ABSTRACT

An X-ray detector according to an embodiment is an X-ray detector configured by arranging a plurality of detector modules, and includes a first detector module, a second detector module, a voltage application circuit, a first transmission circuit, and a first reception circuit. The second detector module is adjacent to the first detector module among the detector modules. The voltage application circuit is disposed in each of the detector modules, and applies a voltage to a plurality of detection elements included in each of the detector modules. The first transmission circuit is disposed in the first detector module, and transmits a signal based on the voltage from the voltage application circuit of the first detector module. The first reception circuit is disposed in the second detector module, and receives a signal transmitted from the first transmission circuit.

16 Claims, 6 Drawing Sheets

(56) References Cited

U.S. PATENT DOCUMENTS

| | | | | |
|---|---|---|---|---|
| 2014/0184383 A1* | 7/2014 | Wodnicki | ............. | A61B 8/4483 |
| | | | | 340/4.3 |
| 2015/0177388 A1* | 6/2015 | Chaudhury | ....... | H01L 27/14676 |
| | | | | 250/370.09 |
| 2017/0290558 A1* | 10/2017 | Kikuchi | ................... | H04N 5/32 |
| 2017/0324280 A1* | 11/2017 | Suzuki | ................ | H04B 5/0037 |
| 2021/0307708 A1* | 10/2021 | Vallgren | .............. | A61B 6/4411 |

* cited by examiner

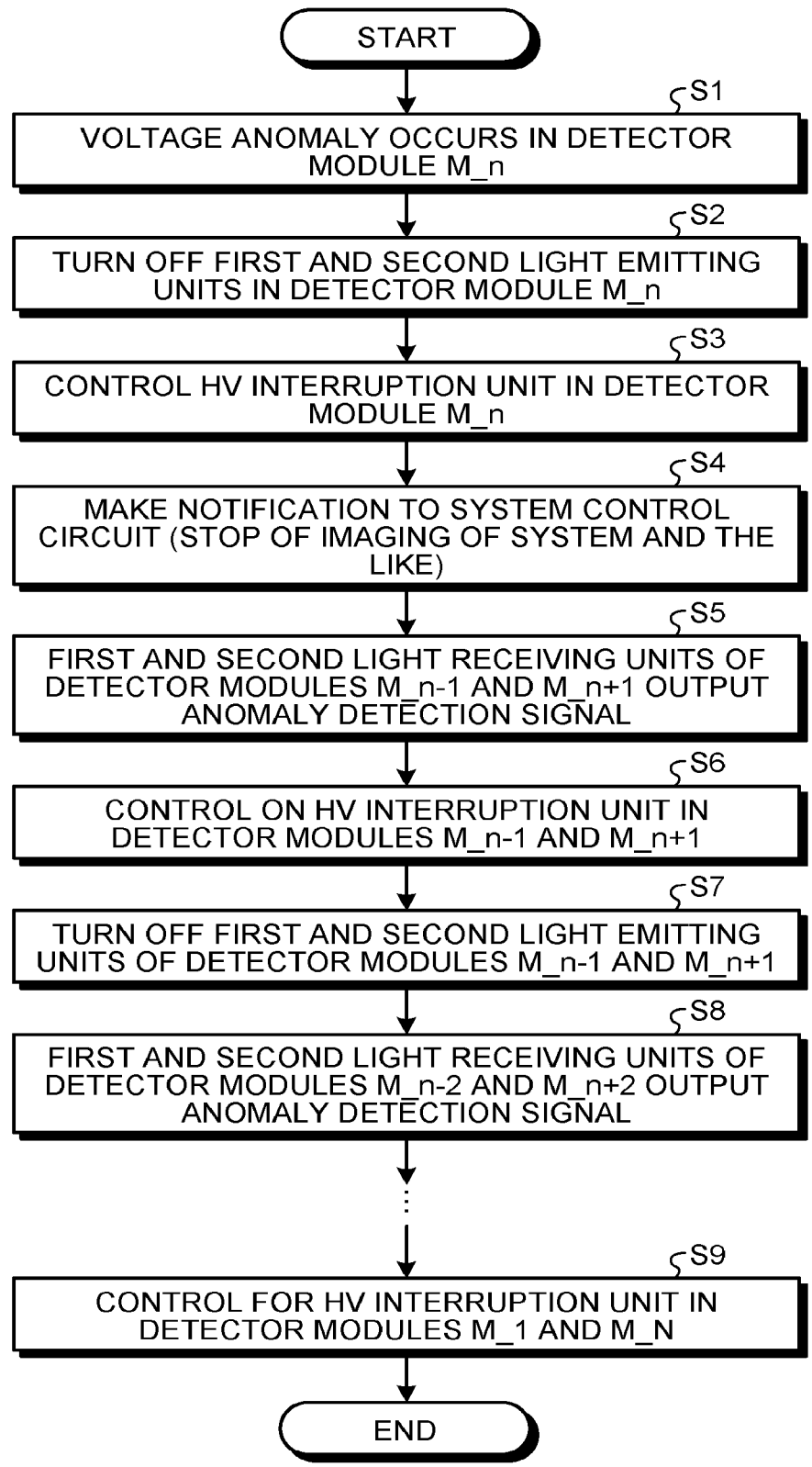

X-RAY DETECTOR AND MEDICAL IMAGE DIAGNOSTIC APPARATUS

CROSS-REFERENCE TO RELATED APPLICATIONS

This application is based upon and claims the benefit of priority from Japanese Patent Application No. 2020-026346, filed on Feb. 19, 2020; the entire contents of which are incorporated herein by reference.

FIELD

Embodiments described herein relate generally to an X-ray detector and a medical image diagnostic apparatus.

BACKGROUND

As an X-ray detector used for X-Ray Computed Tomography (hereinafter, referred to as an "X-ray CT device"), there is known an X-ray detector of a photon counting type (photon counting detector). The photon counting detector catches each incident X-ray as a photon, and counts the number of photons to measure intensity of the X-ray. In the photon counting detector, in converting an X-ray photon into an electric charge, a charge amount corresponding to energy of the X-ray photon is generated. Due to this, an energy spectrum of each X-ray photon can be measured.

Generally, examples of the photon counting detector include a direct type detector and an indirect type detector. The direct type detector is a semiconductor detector using CdTe, CdTeZn (or CZT), and the like, and directly converts an incident X-ray into an electric charge. The indirect type detector uses a scheme of temporarily converting an incident X-ray into visible light by a scintillator.

In the direct type detector, a high voltage (bias voltage) needs to be applied between electrodes of detection elements. The photon counting detector as a plane detector is not limited to the direct type detector, and may include a large number of module-structured detectors being disposed. For example, in the direct type detector, when a high voltage unit of one module breaks down to cause a voltage drop (for example, about 0 V), an electric discharge is caused by a potential difference with respect to an adjacent module, and the adjacent module may break down in some cases. Additionally, when the high voltage unit of the module that has broken down due to the electric discharge drops to about 0 V, an electric discharge is further caused between itself and the adjacent module, and the breakdown may spread to the entire surface of the detector module in the end.

BRIEF DESCRIPTION OF THE DRAWINGS

FIG. 6 is a flowchart for explaining an operation of the X-ray detector and the X-ray CT device according to the embodiment.

DETAILED DESCRIPTION

An X-ray detector according to an embodiment is an X-ray detector that is configured by arranging a plurality of detector modules, and includes a first detector module, a second detector module, a voltage application circuit, a first transmission circuit, and a first reception circuit. The second detector module is adjacent to the first detector module among the detector modules. The voltage application circuit is disposed in each of the detector modules, and applies a voltage to a plurality of detection elements included in each of the detector modules. The first transmission circuit is disposed in the first detector module, and transmits a signal based on the voltage applied by the voltage application circuit of the first detector module. The first reception circuit is disposed in the second detector module, and receives the signal transmitted from the first transmission circuit.

The following describes an X-ray detector and an X-ray CT device according to the embodiment with reference to the drawings.

The X-ray CT device described in the following embodiment is a device that can execute photon counting CT. That is, the X-ray CT device described in the following embodiment is not a conventional detector of an integration type (current mode measuring scheme), but is a device that can reconstruct X-ray CT image data having a high SN ratio by counting X-rays transmitted through a subject using a photon counting detector.

Figure 1:
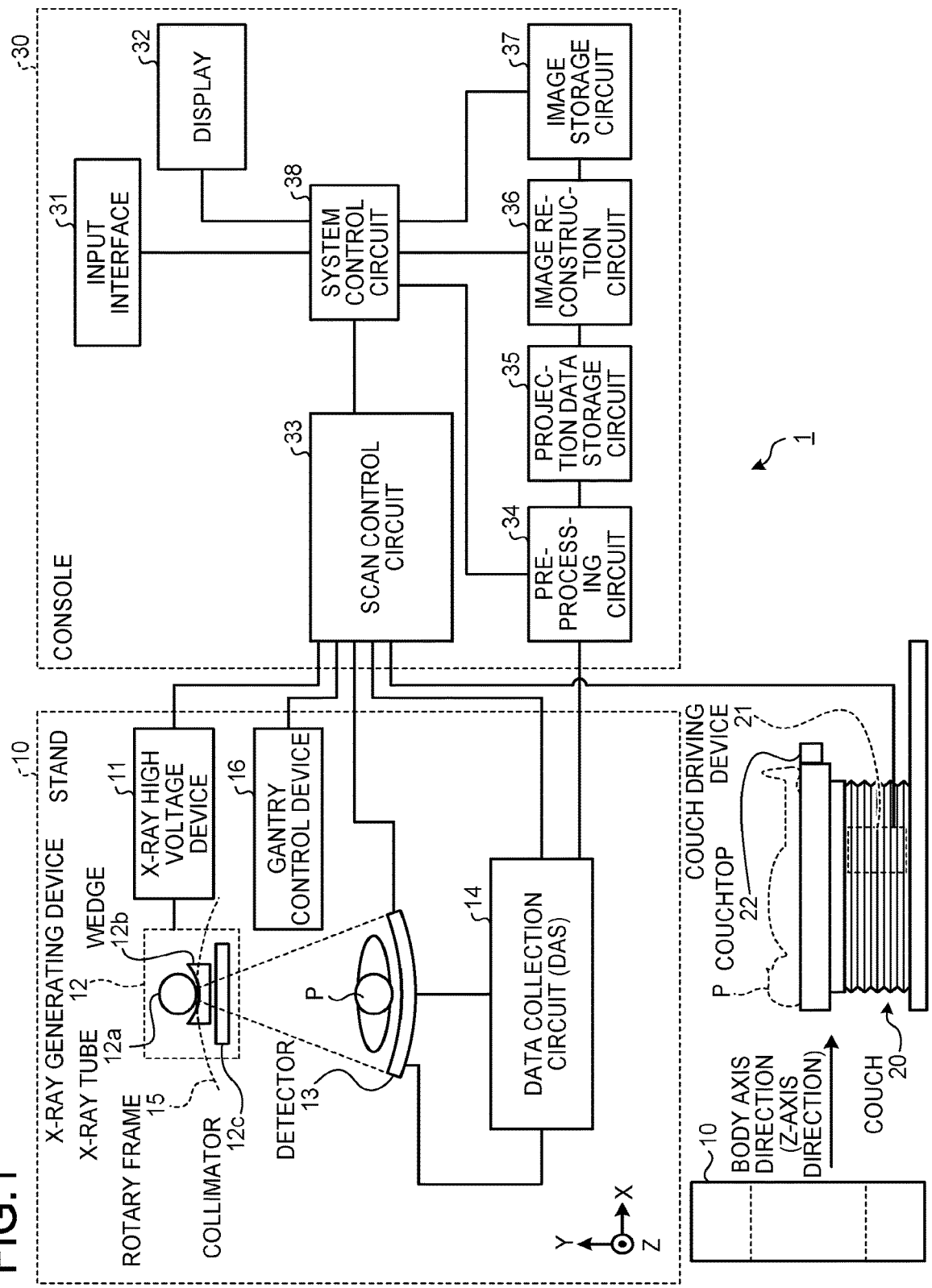
FIG. 1 is a block diagram illustrating a configuration example of an X-ray CT device according to an embodiment.

FIG. 1 is a block diagram illustrating a configuration example of an X-ray CT device 1 according to the embodiment. As illustrated in FIG. 1, the X-ray CT device 1 according to the embodiment includes a gantry 10, a couch 20, and a console 30.

The gantry 10 is a device that irradiates a subject P with X-rays, and collects data related to the X-rays transmitted through the subject P. The gantry 10 includes an X-ray high voltage device 11, an X-ray generating device 12, a detector 13, a data collection circuit 14, a rotary frame 15, and a gantry control device 16.

As illustrated in FIG. 1, an orthogonal coordinate system including an X-axis, a Y-axis, and a Z-axis is defined for the gantry 10. That is, the X-axis indicates a horizontal direction, the Y-axis indicates a vertical direction, and the Z-axis indicates a rotation center axis direction of the rotary frame 15 when the gantry 10 is in a non-tilted state. The detector 13 and the data collection circuit 14 may be formed as a detector unit DU of an integral type in some cases. Typically, wording such as a "detector" and an "X-ray detector" means any of the detector 13 and the detector unit DU. In the present embodiment, for specific description, the detector 13 and the data collection circuit 14 are assumed to form the detector unit DU of an integral-type. However, an inter-module communication control function, an inter-module block control function, and a module-system control function (described later) may be applied to any of the detector 13 as a single item and the detector unit DU of an integral-type including the detector 13 and the data collection circuit 14.

Figure 2:
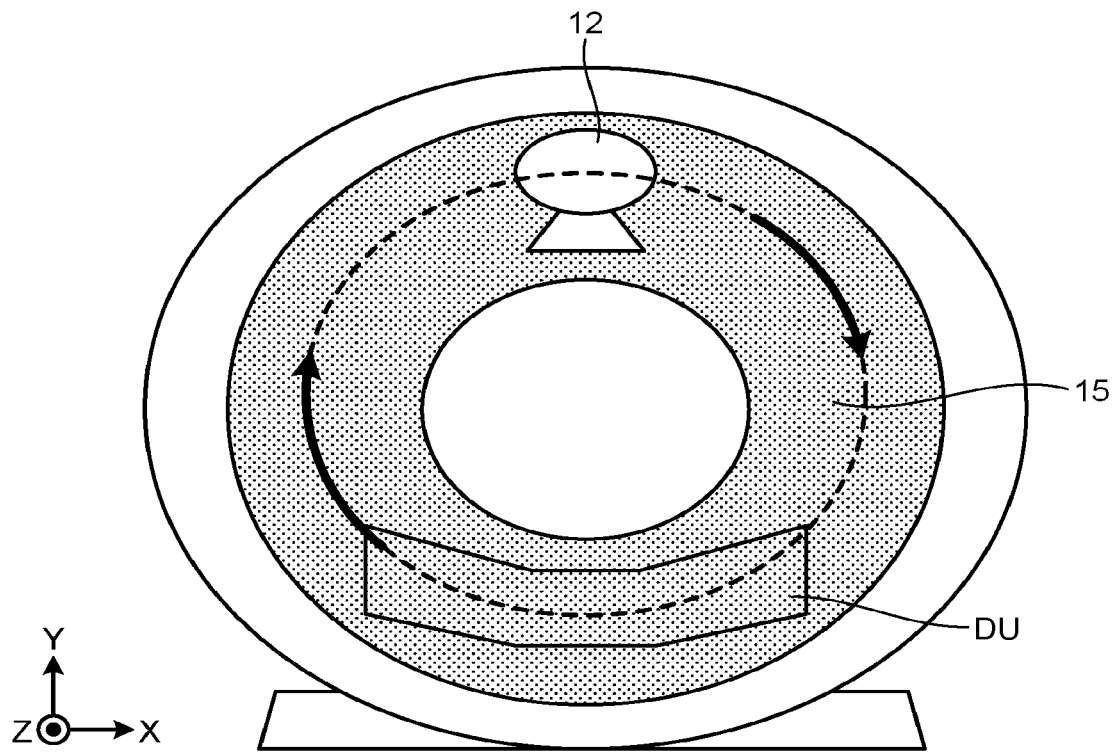
FIG. 2 is a front view of a gantry of the X-ray CT device according to the embodiment.

FIG. 2 is a front view of the gantry 10 according to the embodiment. As illustrated in FIG. 2, the X-ray generating device 12 and the detector unit DU including the detector 13 and the data collection circuit 14 are supported to be opposed to each other across the subject P by the rotary frame 15. The rotary frame 15 is rotated at high speed along a circular orbit centered on the subject P by the gantry control device 16 (described later).

Returning to FIG. 1, the X-ray generating device 12 is a device that generates X-rays, and irradiates the subject P with the generated X-rays. The X-ray generating device 12 includes an X-ray tube 12a, a wedge 12b, and a collimator 12c.

The X-ray tube 12a is a vacuum tube that receives a high voltage supplied from the X-ray high voltage device 11, and emits thermoelectrons to an anode (target) from a cathode (also referred to as a filament in some cases), and irradiates the subject P with an X-ray beam along with rotation of the rotary frame 15. That is, the X-ray tube 12a generates X-rays using the high voltage supplied from the X-ray high voltage device 11.

The X-ray tube 12a also generates an X-ray beam that spreads to have a fan angle and a cone angle. For example, the X-ray tube 12a can continuously emit X-rays over the entire periphery of the subject P for full reconstruction, or can continuously emit X-rays in an emission range (180 degrees+fan angle) in which half reconstruction can be implemented for half reconstruction, under control by the X-ray high voltage device 11. The X-ray tube 12a can also intermittently emit X-rays (pulse X-rays) at a position set in advance (a vacuum tube position) under control by the X-ray high voltage device 11. The X-ray high voltage device 11 can modulate intensity of the X-rays emitted from the X-ray tube 12a. For example, the X-ray high voltage device 11 increases the intensity of the X-rays emitted from the X-ray tube 12a at a specific vacuum tube position, and reduces the intensity of the X-rays emitted from the X-ray tube 12a in a range excluding the specific vacuum tube position.

The wedge 12b is an X-ray filter for adjusting an X-ray dose of the X-rays emitted from the X-ray tube 12a. Specifically, the wedge 12b is a filter that transmits the X-rays emitted from the X-ray tube 12a to be attenuated so that the X-rays emitted from the X-ray tube 12a to the subject P are distributed as determined in advance. For example, the wedge 12b is a filter obtained by processing aluminum to have a predetermined target angle and a predetermined thickness. The wedge is also called a wedge filter or a bow-tie filter.

The collimator 12c is constituted of a lead plate and the like, and has a slit on part thereof. For example, the collimator 12c narrows, by the slit, an irradiation range of the X-rays the X-ray dose of which is adjusted by the wedge 12b under control by the X-ray high voltage device 11 (described later).

An X-ray source of the X-ray generating device 12 is not limited to the X-ray tube 12a. For example, the X-ray generating device 12 may be constituted of a focus coil that focuses an electron beam generated by an electron gun and a deflection coil that electromagnetically deflects the electron beam, and a target ring that surrounds a half periphery of the subject P and generates X-rays by colliding with the deflected electron beam, instead of the X-ray tube 12a.

The X-ray high voltage device 11 is constituted of a high voltage generation device that is constituted of an electric circuit such as a transformer and a rectifier and has a function of generating a high voltage to be applied to the X-ray tube 12a, and an X-ray control device that controls an output voltage corresponding to the X-rays emitted by the X-ray tube 12a. The high voltage generation device may be a transformer type, or an inverter type. For example, the X-ray high voltage device 11 adjusts a tube voltage and a tube current supplied to the X-ray tube 12a to adjust the dose of the X-rays emitted to the subject P. The X-ray high voltage device 11 is controlled by a scan control circuit 33 of the console 30.

The gantry control device 16 is constituted of a processing circuit that is constituted of a central processing unit (CPU) and the like, and a driving mechanism such as a motor and an actuator. The gantry control device 16 has a function of performing operation control on the gantry 10 by receiving an input signal from an input interface 31 attached to the console 30 or an input interface attached to the gantry 10. For example, by receiving the input signal and rotating the rotary frame 15, the gantry control device 16 performs control for turning the X-ray tube 12a and the detector 13 on the circular orbit centered on the subject P, control for tilting the gantry 10, and control for causing the couch 20 and a couchtop 22 to operate. The gantry control device 16 is controlled by the scan control circuit 33 of the console 30.

The gantry control device 16 monitors a position of the X-ray tube 12a. When the X-ray tube 12a reaches a predetermined rotation angle (imaging angle), the gantry control device 16 outputs a view trigger signal indicating a timing for starting to capture data to the data collection circuit 14. For example, in a case in which the total number of views in rotary imaging is 2400 views, the gantry control device 16 outputs the view trigger signal every time the X-ray tube 12a moves along the circular orbit by 0.15 degrees (=360/2400).

The detector 13 is a photon counting detector, and includes a plurality of X-ray detection elements (also referred to as a "sensor", or simply referred to as a "detection element") for counting pieces of light derived from the X-rays transmitted through the subject P. That is, the detector 13 includes the detection elements, and outputs detection signals (electric signals output from the respective X-ray detection elements) corresponding to the number of incident photons. The detector 13 according to the embodiment is a plane detector of a direct type using a semiconductor such as CdTe and CdTeZn (CZT).

The data collection circuit 14 is an electric circuit having a function of collecting counting results as a result of count processing using the detection signals of the detector 13. The data collection circuit 14 collects, as counting results, results obtained by counting photons (X-ray photons) derived from the X-rays that are emitted from the X-ray tube 12a and transmitted through the subject P, and discriminating energy of the counted photons. The data collection circuit 14 then transmits the counting results to the console 30. The data collection circuit 14 is also called a data acquisition system (DAS).

For example, the data collection circuit 14 includes a plurality of application specific integrated circuits (ASICs) and the like. In a case of configuring the detector 13 as a plane detector, the ASIC and the like need to be arranged to be very close to the detector 13 in high density to measure a minute output current from the detector 13.

Figure 3:
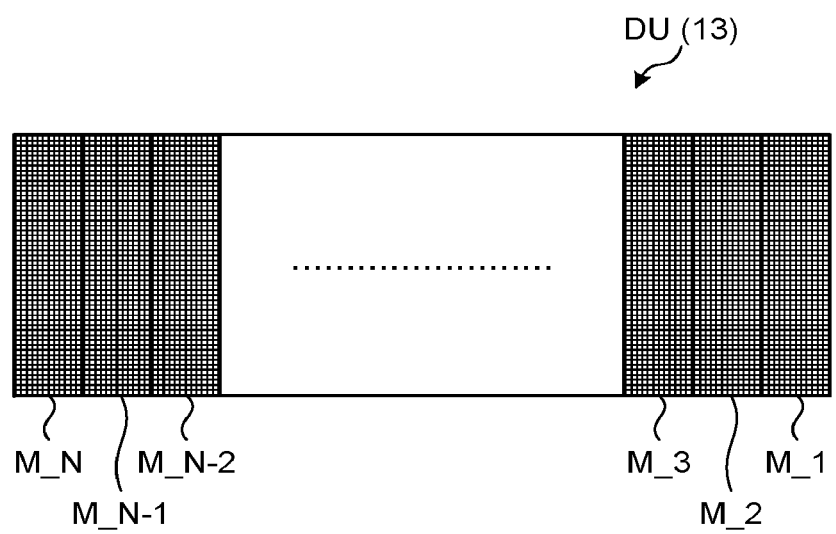
FIG. 3 is a diagram for explaining an example of an X-ray detector according to the embodiment.

FIG. 3 is a diagram for explaining an example of the detector unit DU according to the embodiment, and is a diagram of the detector unit DU (or the detector 13) illustrated in FIG. 2 viewed from an X-ray incident direction (a diagram of the detector unit DU viewed from the Y-axis side). As illustrated in FIG. 3, for example, the detector unit DU is constituted of a plurality of detector modules M_1 to M_N that are densely arranged in the X-axis direction.

Figure 4:
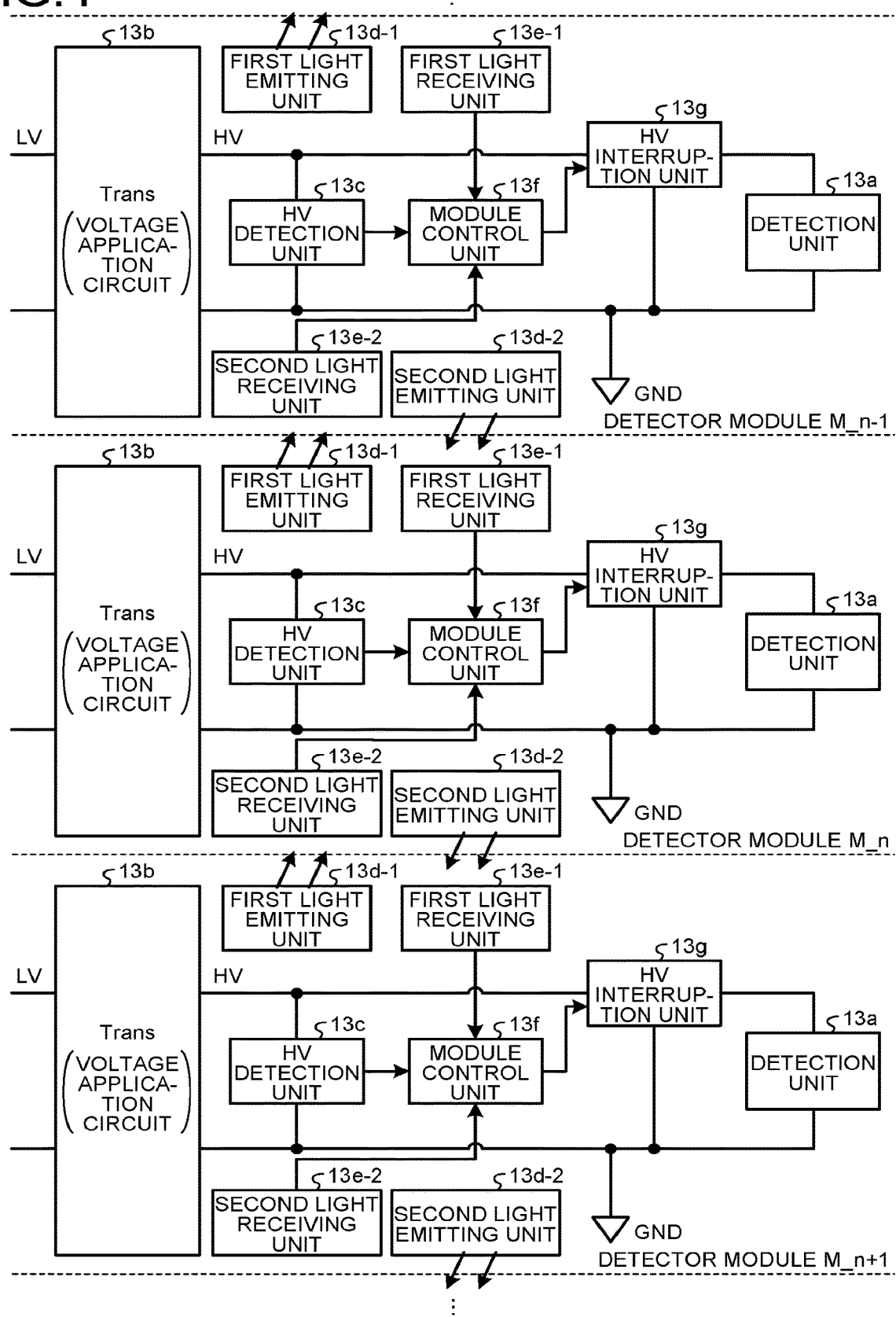
FIG. 4 is a diagram for explaining a configuration of each detector module of the X-ray detector according to the embodiment.

FIG. 4 is a diagram for explaining a configuration of each of the detector modules M_1 to M_N. The detector modules M_1 to M_N have substantially the same configuration. The following describes a configuration of a detector module M_n by way of example.

As illustrated in FIG. 4, the detector module M_n includes a detection unit 13a, a voltage conversion unit 13b, an HV detection unit 13c, a first light emitting unit 13d-1, a first light receiving unit 13e-1, a second light emitting unit 13d-2, a second light receiving unit 13e-2, a module control unit 13f, and an HV interruption unit 13g. The voltage conversion unit 13b corresponds to a voltage application circuit. The first light emitting unit 13d-1 corresponds to a first transmission circuit. The first light receiving unit 13e-1 corresponds to a second reception circuit. The second light emitting unit 13d-2 corresponds to a second transmission circuit. The second light receiving unit 13e-2 corresponds to a first reception circuit. The module control unit 13f corresponds to a module control circuit.

The detection unit 13a includes a plurality of detection elements that are arranged along a channel direction (X-axis direction in FIG. 3) and a body axis (column) direction of the subject P (Z-axis direction illustrated in FIG. 3). By arranging the detector modules M_1 to M_N each including the detection unit 13a in the X-axis direction, the detection elements are arranged in the channel direction and the column direction, and a detection face of the detector unit DU is formed.

The voltage conversion unit 13b applies a voltage (bias voltage) to the detection elements included in each of the detector modules. The voltage conversion unit 13b is a transformer that boosts a low voltage (LV) supplied from a voltage power supply device (not illustrated) to be a high voltage (HV). In the present embodiment, a circuit unit connected to the low voltage (LV) on an input side of the voltage conversion unit 13b is referred to as a low voltage unit LV, and a circuit unit connected to the high voltage (HV) on an output side of the voltage conversion unit 13b is referred to as a high voltage unit HV.

The HV detection unit 13c is a voltage detection circuit that detects the high voltage (HV) on the output side of the voltage conversion unit 13b. In a case in which a value of the high voltage (HV) on the output side of the voltage conversion unit 13b becomes lower than a predetermined reference value (threshold), the HV detection unit 13c outputs, to the module control unit 13f, an anomaly detection signal for notifying that the value of the high voltage (HV) on the output side of the voltage conversion unit 13b is abnormal.

The first light emitting unit 13d-1 and the second light emitting unit 13d-2 transmit a signal (optical signal) based on the voltage from the voltage conversion unit 13b. For example, the first light emitting unit 13d-1 and the second light emitting unit 13d-2 are light emitting elements (for example, photodiodes) that emit light based on electric power obtained by voltage-converting the high voltage (HV). That is, the first light emitting unit 13d-1 and the second light emitting unit 13d-2 are turned on when the high voltage (HV) is a normal value, and turned off when the high voltage (HV) drops to about 0 V, for example. On and off of the first light emitting unit 13d-1 and the second light emitting unit 13d-2 are also controlled by the module control unit 13f.

The first light emitting unit 13d-1 is disposed at a position opposed to the second light receiving unit 13e-2 of an adjacent detector module M_n-1 in a housing of the detector module M_n. The second light emitting unit 13d-2 is disposed at a position opposed to the first light receiving unit 13e-1 of an adjacent detector module M_n+1 (that is, a module opposite to the detector module M_n-1) in the housing of the detector module M_n.

The first light receiving unit 13e-1 receives a signal transmitted from the second light emitting unit 13d-2 of the adjacent detector module M_n-1. For example, the first light receiving unit 13e-1 is a light receiving element (for example, a phototransistor) that receives light. The first light receiving unit 13e-1 is disposed at a position opposed to the second light emitting unit 13d-2 of the adjacent detector module M_n-1 in the housing of the detector module M_n. In a case of not receiving light from the second light emitting unit 13d-2 of the adjacent detector module M_n-1, the first light receiving unit 13e-1 outputs, to the module control unit 13f, an anomaly detection signal for notifying that light is not received.

The second light receiving unit 13e-2 receives a signal transmitted from the first light emitting unit 13d-1 of the adjacent detector module M_n+1. For example, the second light receiving unit 13e-2 is a light receiving element (for example, a phototransistor) that receives light. The second light receiving unit 13e-2 is disposed at a position opposed to the first light emitting unit 13d-1 of the adjacent detector module M_n+1 (that is, a module opposite to the detector module M_n-1) in the housing of the detector module M_n. In a case of not receiving light from the first light emitting unit 13d-1 of the adjacent detector module M_n+1, the second light receiving unit 13e-2 outputs, to the module control unit 13f, an anomaly detection signal for notifying that light is not received.

Figure 5A:
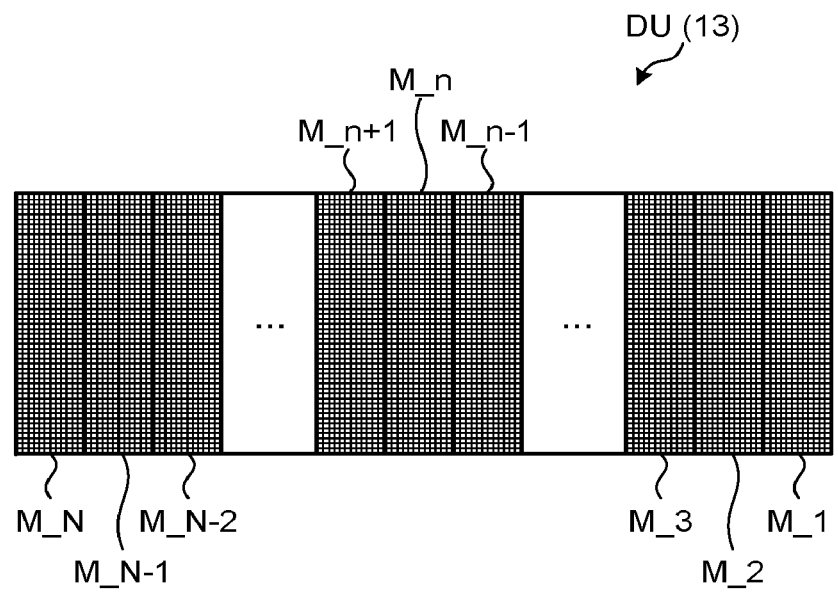
FIG. 5A is a diagram illustrating a plurality of detector modules adjacent to each other.
Figure 5B:
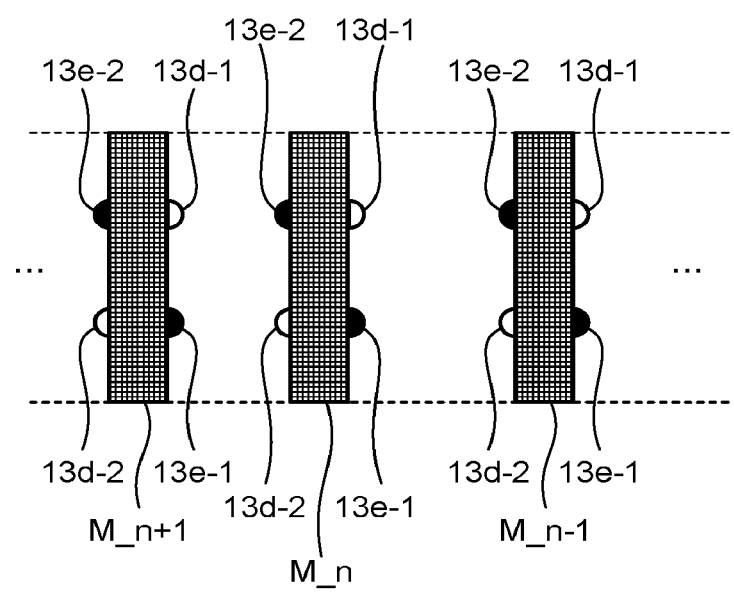
FIG. 5B is a diagram illustrating an arrangement relation between a first light emitting unit and a second light receiving unit, and an arrangement relation between a second light emitting unit and a first light receiving unit between the adjacent detector modules.

FIG. 5A is a diagram illustrating the detector module M_n-1 and the detector module M_n+1 that are adjacent to the detector module M_n in the detector unit DU illustrated in FIG. 3. FIG. 5B is a diagram illustrating an arrangement relation between the first light emitting unit 13d-1 and the second light receiving unit 13e-2, and an arrangement relation between the second light emitting unit 13d-2 and the first light receiving unit 13e-1 in the detector module M_n-1, the detector module M_n, and the detector module M_n+1. In FIG. 5B, a gap of a fixed size is illustrated between the detector module M_n-1 and the detector module M_n, and between the detector module M_n and the detector module M_n+1. This gap is disposed for convenience' sake to explain the arrangement relation between the first light emitting unit 13d-1 and the second light receiving unit 13e-2, and the arrangement relation between the second light emitting unit 13d-2 and the first light receiving unit 13e-1. As described above, the detector modules M_1 to M_N are densely arranged as illustrated in FIG. 3 and FIG. 5A. Thus, the gap between the detector modules illustrated in FIG. 5B is not present in the actual detector unit DU.

As illustrated in FIG. 5B, the first light emitting unit 13d-1 of the detector module M_n is arranged to correspond to the second light receiving unit 13e-2 of the detector module M_n-1. Thus, in a case in which the first light emitting unit 13d-1 of the detector module M_n is turned off for some reason (for example, in a case in which the voltage of the high voltage unit HV of the detector module M_n becomes 0 V), the second light receiving unit 13e-2 of the detector module M_n-1 does not receive light from the first light emitting unit 13d-1 of the detector module M_n.

Similarly, as illustrated in FIG. 5B, the second light emitting unit 13d-2 of the detector module M_n-1 is arranged to correspond to the first light receiving unit 13e-1 of the detector module M_n. Thus, in a case in which the second light emitting unit 13d-2 of the detector module M_n−1 is turned off for some reason (for example, in a case in which the voltage of the high voltage unit HV of the detector module M_n−1 becomes 0 V), the first light receiving unit 13e-1 of the detector module M_n does not receive light from the second light emitting unit 13d-2 of the detector module M_n−1.

The first light receiving unit 13e-1 of the detector module M_1 and the second light receiving unit 13e-2 of the detector module M_N are adjacent to a wall of a housing of the detector 13. Due to this, the second light emitting unit 13d-2 opposed to the first light receiving unit 13e-1 of the detector module M_1 is disposed on the wall of the detector 13 that is adjacent to the detector module M_1. The first light emitting unit 13d-1 opposed to the second light receiving unit 13e-2 of the detector module M_N is disposed on the wall of the detector 13 that is adjacent to the detector module M_N. With this configuration, the first light receiving unit 13e-1 of the detector module M_1 and the second light receiving unit 13e-2 of the detector module M_N are kept in a light receiving state at all times, and prevented from erroneously outputting the anomaly detection signal. Additionally, with this configuration, all of the detector module M_1 to the detector module M_N can be caused to have the same configuration. Alternatively, the configuration may be made such that the first light receiving unit 13e-1 of the detector module M_1 and the second light receiving unit 13e-2 of the detector module M_N are not disposed, or the first light receiving unit 13e-1 of the detector module M_1 and the second light receiving unit 13e-2 of the detector module M_N do not generate the anomaly detection signal.

Returning to FIG. 4, the module control unit 13f is a processing circuit such as a processor. The module control unit 13f controls an HV interruption unit 13g in response to the anomaly detection signal received from the HV detection unit 13c, and controls a voltage supplied from the voltage conversion unit 13b to the detection unit 13a. For example, the module control unit 13f controls the HV interruption unit 13g in response to the anomaly detection signal received from the HV detection unit 13c, and connects (interrupts) the voltage applied from the voltage conversion unit 13b to GND. Alternatively, the module control unit 13f can control the HV interruption unit 13g in response to the anomaly detection signal received from the HV detection unit 13c, and switch the voltage applied from the voltage conversion unit 13b to be a low voltage with which an electric discharge is not caused. Note that the module control unit 13f is an example of a first control circuit or a first control unit.

The module control unit 13f also turns off the first light emitting unit 13d-1 and the second light emitting unit 13d-2 in response to the anomaly detection signal received from the HV detection unit 13c. The module control unit 13f turns off the first light emitting unit 13d-1 and the second light emitting unit 13d-2 in response to the anomaly detection signal received from any of the first light receiving unit 13e-1 and the second light receiving unit 13e-2.

The module control unit 13f also outputs the anomaly detection signal for notifying that an anomaly occurs in the module to the system control circuit 38 of the X-ray CT device 1 in response to the anomaly detection signal received from the HV detection unit 13c. Note that the module control unit 13f is an example of a second control circuit or a second control unit.

The HV interruption unit 13g is a switch (for example, a switching element such as a MOSFET, a thyristor, and an IGBT) or the like that is disposed between the voltage conversion unit 13b and the detection unit 13a to interrupt connection between the voltage conversion unit 13b and the detection unit 13a in response to a control signal from the module control unit 13f. The HV interruption unit 13g switches the voltage supplied to the detection unit 13a from the high voltage (HV) to GND in response to a control signal (interruption ON signal) from the module control unit 13f. Alternatively, in response to the control signal from the module control unit 13f, the HV interruption unit 13g can switch the voltage supplied from the voltage conversion unit 13b to the detection unit 13a from the high voltage (HV) to the low voltage with which an electric discharge is not caused.

Returning to FIG. 1, the couch 20 is a device on which the subject P is placed, and includes a couchtop 22 and a couch driving device 21. The couchtop 22 is a plate on which the subject P is placed, and the couch driving device 21 moves the couchtop 22 in the Z-axis direction to move the subject P into the rotary frame 15. The couch driving device 21 can also move the couchtop 22 in the X-axis direction.

As a method of moving the couchtop, only the couchtop 22 may be moved, or a base of the couch 20 may be moved together. In a case of CT in a gantrying position, a patient moving mechanism corresponding to the couchtop 22 may be moved.

For example, the gantry 10 performs helical scanning for helically scanning the subject P while moving the couchtop 22 and rotating the rotary frame 15. Alternatively, the gantry 10 performs conventional scanning for scanning the subject P along a circular orbit while fixing the position of the subject P and rotating the rotary frame 15 after moving the couchtop 22.

In the following embodiment, relative positions of the gantry 10 and the couchtop 22 are assumed to be changed by controlling the couchtop 22, but the embodiment is not limited thereto. For example, in a case in which the gantry 10 is a self-propelled type, the relative positions of the gantry 10 and the couchtop 22 may be changed by controlling traveling of the gantry 10. Alternatively, the relative positions of the gantry 10 and the couchtop 22 may be changed by controlling traveling of the gantry 10 and the couchtop 22.

The console 30 is a device that receives an operation on the X-ray CT device by an operator, and reconstructs X-ray CT image data using the counting results collected by the gantry 10. As illustrated in FIG. 1, the console 30 includes the input interface 31, a display 32, the scan control circuit 33, a pre-processing circuit 34, a projection data storage circuit 35, an image reconstruction circuit 36, an image storage circuit 37, and a system control circuit 38.

The input interface 31 includes a mouse, a keyboard, and the like used by the operator of the X-ray CT device for inputting various instructions and various settings, and transfers information about instructions and settings received from the operator to the system control circuit 38. For example, the input interface 31 receives a reconstruction condition for reconstructing the X-ray CT image data, an image processing condition for the X-ray CT image data, and the like from the operator.

The display 32 is a monitor that is referred to by the operator. The display 32 displays the X-ray CT image data to the operator, or displays a graphical user interface (GUI) for receiving various instructions, various settings, and the like from the operator via the input interface 31 under control by the system control circuit 38.

The scan control circuit 33 is an electric circuit having a function of controlling collection processing for the counting results performed by the gantry 10 by controlling operations of the X-ray high voltage device 11, the detector 13, the gantry control device 16, the data collection circuit 14, and the couch driving device 21 under control by the system control circuit 38 (described later).

The pre-processing circuit 34 is an electric circuit having a function of generating raw data by performing pre-processing such as logarithm conversion processing, offset correction processing, inter-channel sensitivity correction processing, inter-channel gain correction processing, pile-up correction processing, response function correction processing, beam hardening correction, and the like on the counting results transmitted from the data collection circuit 14.

The projection data storage circuit 35 is, for example, a NAND (Not AND) type flash memory or a hard disk drive (HDD), and stores projection data generated by the pre-processing circuit 34. That is, the projection data storage circuit 35 stores projection data for reconstructing the X-ray CT image data.

The image reconstruction circuit 36 performs reconstruction processing using a filtered back projection method, a successive approximation reconstruction method, and the like on the projection data generated by the pre-processing circuit 34 to generate the X-ray CT image data.

The image reconstruction circuit 36 stores the reconstructed X-ray CT image data in the image storage circuit 37.

In this case, the projection data generated from the counting results obtained by photon counting CT includes information about energy of X-rays attenuated by being transmitted through the subject P. Due to this, for example, the image reconstruction circuit 36 can reconstruct the X-ray CT image data of a specific energy component. The image reconstruction circuit 36 can also reconstruct the X-ray CT image data of each of a plurality of energy components, for example.

For example, the image reconstruction circuit 36 assigns a color tone corresponding to the energy component to each pixel of the X-ray CT image data of each of the energy components, and generates image data obtained by superimposing a plurality of pieces of the X-ray CT image data on each other, the pieces of the X-ray CT image data being classified by color corresponding to the energy component. For example, the image reconstruction circuit 36 can also use a K-absorption edge unique to a substance to generate image data with which the substance can be identified. Examples of other image data generated by the image reconstruction circuit 36 include a monochrome X-ray image data, density image data, effective atomic number image data, and the like.

As an application of X-ray CT, there is known a technique of discriminating classifications, abundance, densities, and the like of substances included in the subject P by using the fact that absorption characteristics of the X-rays are different for each substance. This technique is called substance discrimination. For example, the image reconstruction circuit 36 performs substance discrimination on projection data to obtain substance discrimination information. The image reconstruction circuit 36 then reconstructs a substance discrimination image using the substance discrimination information as a result of substance discrimination.

The image reconstruction circuit 36 can apply a full-scan reconstruction scheme and a half-scan reconstruction scheme to reconstruct the CT image. For example, the image reconstruction circuit 36 requires projection data of the entire periphery of the subject P corresponding to 360 degrees for the full-scan reconstruction scheme. The image reconstruction circuit 36 requires projection data corresponding to "180 degrees+fan angle" for the half-scan reconstruction scheme. In the following description, for simplifying the description, the image reconstruction circuit 36 is assumed to use the full-scan reconstruction scheme of performing reconstruction using the projection data of the entire periphery of the subject P corresponding to 360 degrees.

The system control circuit 38 is an electric circuit having a function of performing overall control for the X-ray CT device by controlling operations of the gantry 10, the couch 20, and the console 30. Specifically, the system control circuit 38 controls the scan control circuit 33 to control CT scan performed by the gantry 10. The system control circuit 38 also controls the pre-processing circuit 34 or the image reconstruction circuit 36 to control image reconstruction processing or image generation processing performed by the console 30. The system control circuit 38 performs control so that various pieces of image data stored in the image storage circuit 37 are displayed on the display 32. The image storage circuit 37 is, for example, a NAND type flash memory or an HDD, and stores various pieces of image data.

The system control circuit 38 also stops imaging, moves the couch to a safe position, and notifies a user that an anomaly occurs in response to the anomaly detection signal received from the module control unit 13f of the detector module.

Inter-Module Communication Control Function

Next, the following describes an inter-module communication control function of the X-ray detector and the X-ray CT device according to the present embodiment. The inter-module communication control function is implemented such that adjacent modules monitor presence/absence of a circuit anomaly each other by communication functions of the adjacent modules, and in a case in which an anomaly (typically, a breakdown of the voltage conversion unit 13b, a voltage drop caused by a short circuit of a circuit, and the like) occurs in the adjacent module, the module in which the anomaly occurs quickly conveys the fact that the anomaly occurs to the adjacent module.

The following describes the inter-module communication control function with reference to FIG. 4.

For example, in FIG. 4, assumed is a case in which the high voltage unit (HV) breaks down and a voltage drop is caused in the detector module M_n (an example of the first detector module), and the voltage at the high voltage unit (HV) drops to about 0 V, for example. In such a case, the HV detection unit 13c outputs an anomaly detection signal to the module control unit 13f in response to the voltage drop, and the first light emitting unit 13d-1 and the second light emitting unit 13d-2 disappear.

In the detector module M_n−1 (an example of the second detector module) adjacent to the detector module M_n, the second light receiving unit 13e-2 outputs the anomaly detection signal to the module control unit 13f in response to turning off of the first light emitting unit 13d-1 of the detector module M_n. As illustrated in FIG. 4, the module control unit 13f turns off the first light emitting unit 13d-1 and the second light emitting unit 13d-2 in response to the anomaly detection signal received from the second light receiving unit 13e-2.

In the detector module M_n+1 adjacent to the detector module M_n (that is, an example of the second detector module opposite to the detector module M_n−1), the first light receiving unit 13e-1 outputs the anomaly detection signal to the module control unit 13f in response to turning off of the second light emitting unit 13d-2 of the detector module M_n. As illustrated in FIG. 4, the module control unit 13*f* turns off the first light emitting unit 13*d*-1 and the second light emitting unit 13*d*-2 in response to the anomaly detection signal received from the first light receiving unit 13*e*-1.

Furthermore, in each of the detector module M_n−2 adjacent to the detector module M_n−1 and the detector module M_n+2 adjacent to the detector module M_n+1, the same control is successively performed. Finally, turning off of the first light emitting unit 13*d*-1 and the second light emitting unit 13*d*-2 following the voltage drop in the detector module M_n extends to all of the detector modules M_1 to M_N of the detector unit DU in a series.

That is, the detector modules M_1 to M_N monitor voltage states of the adjacent modules each other by the inter-module communication control function described above. In a case in which a voltage anomaly occurs in any of the modules, the module adjacent to the module in which the voltage anomaly occurs can grasp the fact that the voltage anomaly occurs in the module adjacent thereto on one side, and can notify the module adjacent thereto on the other side that the voltage anomaly occurs, by optical communication. In that sense, light from the first light emitting unit 13*d*-1 and the second light emitting unit 13*d*-2 serves as a signal indicating presence/absence of an anomaly in each module. Such communication by the optical signal between the adjacent modules is performed in a series, and finally, all of the detector modules M_1 to M_N can be notified that the voltage anomaly occurs.

Inter-Module Block Control Function

Next, the following describes the inter-module block control function of the X-ray detector and the X-ray CT device according to the present embodiment. The inter-module block control function is implemented such that, in a case in which a voltage anomaly in a certain module is conveyed to each of the modules by the inter-module communication control function, each module interrupts (momentarily interrupts) supply of the high voltage from the high voltage unit (HV) to each detection element to block an electric discharge between the modules at high speed.

The following describes the inter-module block control function with reference to FIG. 4.

For example, in FIG. 4, assumed is a case in which the high voltage unit (HV) breaks down and a voltage drop is caused in the detector module M_n (that is an example of a first detector module), and the voltage at the high voltage unit (HV) drops to about 0 V, for example. In such a case, the HV detection unit 13*c* outputs the anomaly detection signal to the module control unit 13*f* in response to the voltage drop, and the first light emitting unit 13*d*-1 and the second light emitting unit 13*d*-2 disappear.

In the detector module M_n, the module control unit 13*f* controls the HV interruption unit 13*g* in response to the anomaly detection signal received from the HV detection unit 13*c*, and interrupts voltage supply from the voltage conversion unit 13*b* to the detection unit 13*a*.

In the detector module M_n−1 adjacent to the detector module M_n (that is an example of a second detector module), the second light receiving unit 13*e*-2 outputs the anomaly detection signal to the module control unit 13*f* in response to turning off of the first light emitting unit 13*d*-1 of the detector module M_n. The module control unit 13*f* controls the HV interruption unit 13*g* in response to the received anomaly detection signal, and interrupts voltage supply from the voltage conversion unit 13*b* to the detection unit 13*a*.

In the detector module M_n+1 adjacent to the detector module M_n (that is an example of a second detector module opposite to the detector module M_n−1), the first light receiving unit 13*e*-1 outputs the anomaly detection signal to the module control unit 13*f* in response to turning off of the second light emitting unit 13*d*-2 of the detector module M_n. The module control unit 13*f* controls the HV interruption unit 13*g* in response to the received anomaly detection signal, and interrupts the voltage supply from the voltage conversion unit 13*b* to the detection unit 13*a*.

Furthermore, in each of the detector module M_n−2 adjacent to the detector module M_n−1 and the detector module M_n+2 adjacent to the detector module M_n+1, the same control is successively performed. That is, the voltage anomaly is notified in a series by the inter-module communication control function, and each module controls the voltage from the voltage conversion unit 13*b* to the detection unit 13*a* in conjunction with the serial notifications. Finally, in response to the voltage drop in the detector module M_n that is conveyed in a series by the inter-module communication control function, the voltage supply from the voltage conversion unit 13*b* to the detection unit 13*a* is interrupted in all of the detector modules M_1 to M_N. This interruption is momentary interruption that is successively performed in several hundred usec or less, so that a high-speed electric discharge event can be handled therewith.

Module-System Control Function

Next, the following describes a module-system control function of the X-ray detector and the X-ray CT device according to the present embodiment. The module-system control function is implemented such that the module control unit 13*f* of the detector module M_n in which a breakdown occurs first outputs the anomaly detection signal for notifying that the anomaly occurs in the module to the system control circuit 38 of the X-ray CT device 1 in response to the anomaly detection signal received from the HV detection unit 13*c*. The system control circuit 38 that has received the anomaly detection signal stops imaging, moves the couch to a safe position, and notifies the user that the anomaly occurs.

Operations of X-Ray Detector 13 and X-Ray CT Device 1

Next, the following describes operations of the X-ray detector 13 and the X-ray CT device 1.

FIG. 6 is a flowchart for explaining the operations of the X-ray detector 13 and the X-ray CT device 1 in a case in which a voltage anomaly occurs in the detector module M_n. As illustrated in FIG. 6, first, it is assumed that a voltage anomaly (for example, a voltage drop caused by a breakdown of the voltage conversion unit 13*b*) has occurred in the detector module M_n (Step S1).

In such a case, in the detector module M_n, the first light emitting unit 13*d*-1 and the second light emitting unit 13*d*-2 are turned off along with the voltage drop in the voltage conversion unit 13*b* (Step S2). The HV detection unit 13*c* outputs the anomaly detection signal to the module control unit 13*f*. The module control unit 13*f* controls the HV interruption unit 13*g* in response to the anomaly detection signal from the HV detection unit 13*c*, and interrupts the voltage supply from the voltage conversion unit 13*b* to the detection unit 13*a*, for example (Step S3).

The module control unit 13*f* of the detector module M_n outputs the anomaly detection signal for notifying that the voltage anomaly occurs to the system control circuit 38 of the X-ray CT device 1. The system control circuit 38 of the X-ray CT device 1 stops imaging, moves the couch to a safe position, and notifies the user that the anomaly occurs in response to the received anomaly detection signal (Step S4).

As the first light emitting unit 13*d*-1 of the detector module M_n is turned off, the second light receiving unit 13e-2 of the detector module M_n−1 outputs the anomaly detection signal to the module control unit 13f of the detector module M_n−1. As the second light emitting unit 13d-2 of the detector module M_n is turned off, the first light receiving unit 13e-1 of the detector module M_n+1 outputs the anomaly detection signal to the module control unit 13f of the detector module M_n+1 (Step S5).

In the detector module M_n−1, the module control unit 13f controls the HV interruption unit 13g in response to the anomaly detection signal, and interrupts the voltage supply from the voltage conversion unit 13b to the detection unit 13a, for example. In the detector module M_n+1, the module control unit 13f controls the HV interruption unit 13g in response to the anomaly detection signal, and interrupts the voltage supply from the voltage conversion unit 13b to the detection unit 13a, for example (Step S6).

In the detector module M_n−1, the module control unit 13f turns off the first light emitting unit 13d-1 and the second light emitting unit 13d-2 in response to the anomaly detection signal. In the detector module M_n+1, the module control unit 13f turns off the first light emitting unit 13d-1 and the second light emitting unit 13d-2 in response to the anomaly detection signal (Step S7).

As the first light emitting unit 13d-1 of the detector module M_n−1 is turned off, the second light receiving unit 13e-2 of the detector module M_n−2 outputs the anomaly detection signal to the module control unit 13f of the detector module M_n−2. As the second light emitting unit 13d-2 of the detector module M_n+1 is turned off, the first light receiving unit 13e-1 of the detector module M_n+2 outputs the anomaly detection signal to the module control unit 13f of the detector module M_n+2 (Step S8). Thereafter, the pieces of processing at Steps S5 to S8 are performed in a series for the adjacent detector modules.

Finally, in the detector module M_1, the module control unit 13f controls the HV interruption unit 13g in response to the anomaly detection signal, and interrupts the voltage supply from the voltage conversion unit 13b to the detection unit 13a, for example (Step S9). In the detector module M_N, the module control unit 13f controls the HV interruption unit 13g in response to the anomaly detection signal, and interrupts the voltage supply from the voltage conversion unit 13b to the detection unit 13a, for example (Step S9).

As described above, for example, in a case in which an anomaly (a voltage drop and the like) occurs in the voltage conversion unit 13b in the detector module M_n, the first light emitting unit 13d-1 of the detector module M_n does not transmit a signal based on the voltage of the voltage conversion unit 13b to the second light receiving unit 13e-2 of the adjacent detector module M_n−1 (is turned off). Accordingly, the second light receiving unit 13e-2 of the detector module M_n−1 does not receive the optical signal from the first light emitting unit 13d-1 of the detector module M_n. Due to this, the voltage anomaly occurred in the detector module M_n can be conveyed to the adjacent detector module M_n−1 by optical communication.

Similarly, in a case in which an anomaly (a voltage drop and the like) occurs in the voltage conversion unit 13b in the detector module M_n, the second light emitting unit 13d-2 of the detector module M_n does not transmit a signal based on the voltage of the voltage conversion unit 13b to the first light receiving unit 13e-1 of the adjacent detector module M_n+1 (is turned off). Accordingly, the first light receiving unit 13e-1 of the detector module M_n+1 does not receive the optical signal from the second light emitting unit 13d-2 of the detector module M_n. Due to this, the voltage anomaly occurred in the detector module M_n can be conveyed to the adjacent detector module M_n+1 by optical communication.

The X-ray detector 13 and the X-ray CT device 1 according to the present embodiment further include module control units 13f disposed in the detector modules M_n−1 and M_n+1. The module control unit 13f of the detector module M_n−1 controls application of the voltage to the detection unit 13a by the voltage conversion unit 13b in the detector module M_n−1 in a case in which the second light receiving unit 13e-2 does not receive the signal. Similarly, the module control unit 13f of the detector module M_n+1 controls application of the voltage to the detection unit 13a by the voltage conversion unit 13b in the detector module M_n+1 in a case in which the first light receiving unit 13e-1 does not receive the signal.

That is, in a case in which an anomaly occurs in the voltage conversion unit 13b in the adjacent detector module M_n, the module control units 13f of the detector modules M_n−1 and M_n+1 can control the voltage supplied to the detection unit 13a by the voltage conversion unit 13b in the detector modules M_n−1 and M_n+1 in response to the anomaly by optical communication. As a result, it is possible to suppress an electric discharge caused between the detector module M_n and the detector modules M_n−1 and M_n+1, and a series of electric discharges caused between the adjacent detector modules following the former electric discharge.

As a result, in a case in which the voltage conversion unit 13b breaks down and the like, a series of breakdowns can be suppressed, and downtime of the system can be shortened as much as possible. Additionally, it is sufficient to replace only the detector module M_n as a first broken-down module, so that maintenance cost can be reduced.

Momentary interruption of the high voltage of the module control unit 13f in the detector modules M_n−1 and M_n+1, and momentary interruption of the high voltage in the detector modules following thereto can be successively performed in several hundred usec or less. Thus, a series of electric discharges can be suppressed before an electric discharge as a high-speed event occurs. Such a configuration is especially effective for a module configuration not including a backplane, for example.

In the X-ray detector 13 and the X-ray CT device 1 according to the present embodiment, in a case in which the first light emitting unit 13d-1 does not transmit a signal (is turned off) in the detector module M_n, the module control unit 13f of the detector module M_n transmits the anomaly detection signal to the system control circuit 38 of the X-ray CT device 1. The system control circuit 38 of the X-ray CT device 1 stops imaging, moves the couch to a safe position, and notifies the user that the anomaly occurs in response to the received anomaly detection signal.

Accordingly, safety of a patient can be secured, and a quick action to a breakdown can be promoted without causing unnecessary exposure.

First Modification

The embodiment described above exemplifies a case in which the first light emitting unit 13d-1 and the second light emitting unit 13d-2 are turned off along with the voltage drop in the voltage conversion unit 13b. Alternatively, the first light emitting unit 13d-1 and the second light emitting unit 13d-2 may be turned off based on a result of threshold processing on the voltage of the voltage conversion unit 13b, and communication control between the modules may be performed.

Figure 7:
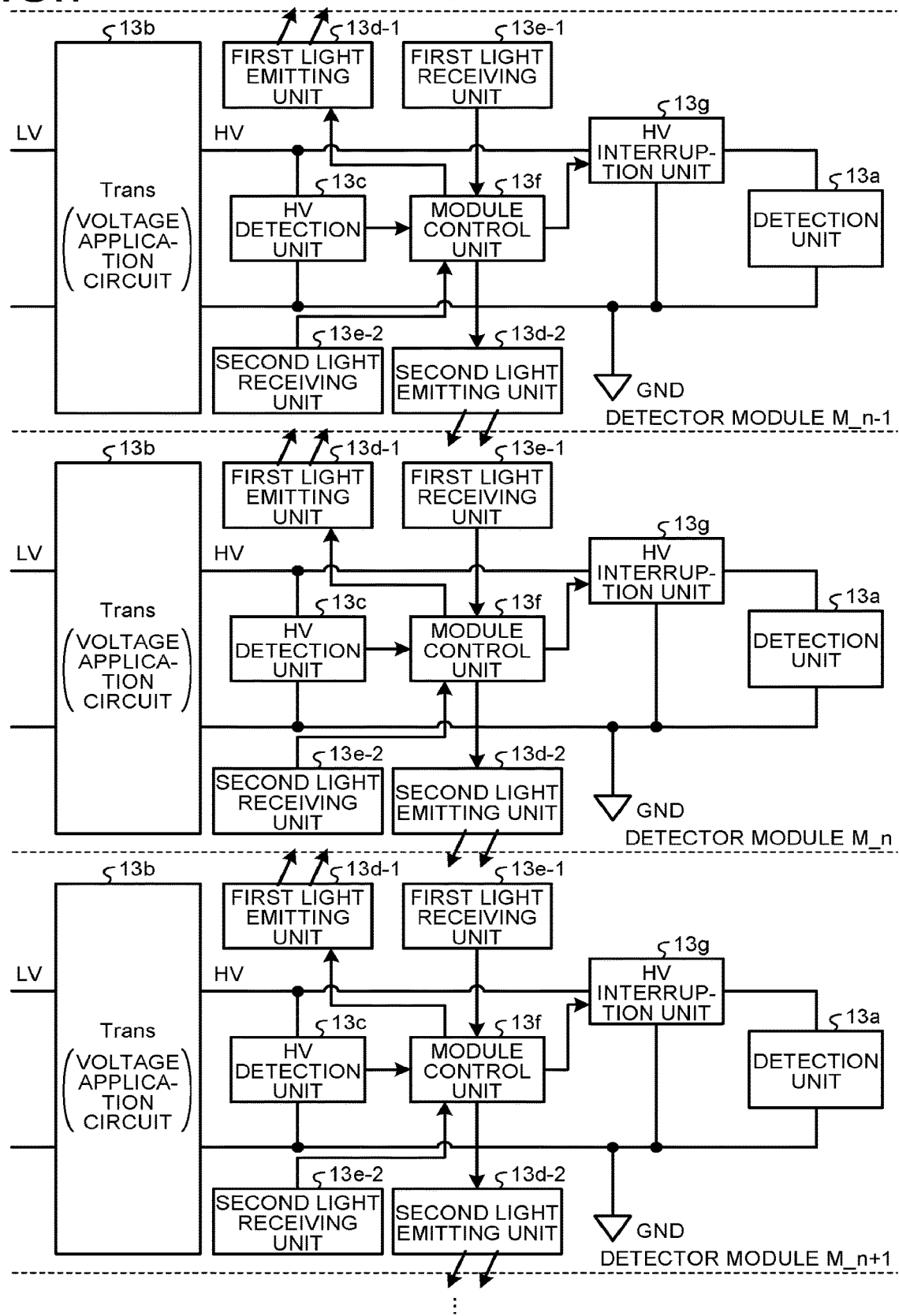
FIG. 7 is a diagram for explaining a configuration of each detector module of an X-ray detector according to a first modification.

FIG. 7 is a diagram for explaining a configuration of each detector module of the X-ray detector according to a first modification. In FIG. 7, the HV detection unit 13c monitors the voltage of the voltage conversion unit 13b, and outputs the anomaly detection signal to the module control unit 13f in a case in which the voltage becomes equal to or lower than a threshold. In this case, the threshold used for comparison with a value of HV can be variable.

The module control unit 13f turns off the first light emitting unit 13d-1 and the second light emitting unit 13d-2 in response to the anomaly detection signal received from the HV detection unit 13c.

Along with variation in the voltage of the voltage conversion unit 13b, an amount of light from the first light emitting unit 13d-1 and the second light emitting unit 13d-2 can be adjusted to control the voltage of the voltage conversion unit 13b in the other detector module.

That is, in FIG. 7, the HV detection unit 13c outputs the detected voltage conversion unit 13b to the module control unit 13f, and the module control unit 13f controls the amount of light from the first light emitting unit 13d-1 and the second light emitting unit 13d-2 in response to the anomaly detection signal received from the HV detection unit 13c. Due to an inter-module communication function, variation in the amount of light from the first light emitting unit 13d-1 and the second light emitting unit 13d-2 in one detector module impacts on all of the other detector modules. In each detector module, the module control unit 13f can control the voltage of the voltage conversion unit 13b in response to the amount of light received by the first light receiving unit 13e-1 and the second light receiving unit 13e-2.

Second Modification

In the embodiment described above, by disposing a storage circuit (a register as a storage unit) that stores presence/absence of the anomaly detection signal from the first light receiving unit 13e-1 and the second light receiving unit 13e-2, for example, in each module control unit 13f of the detector modules M_1 to M_N, the detector module in which a voltage anomaly first occurs can be specified.

For example, in the example illustrated in FIG. 4, in the detector module M_n as a first broken-down module, the anomaly detection signal from the first light receiving unit 13e-1 and the second light receiving unit 13e-2 is not stored in the storage circuit of the module control unit 13f due to the breakdown. On the other hand, in the other detector modules, the HV interruption unit 13g is controlled by the module control unit 13f by the inter-module block control function. Thus, by checking presence/absence of the anomaly detection signal from the first light receiving unit 13e-1 and the second light receiving unit 13e-2 written in the storage circuit that is disposed in each of the detector modules M_1 to M_N, it is possible to specify the detector module in which the voltage anomaly has occurred.

Third Modification

The embodiment described above exemplifies a case of using optical communication between the adjacent detector modules as the inter-module communication control function. Alternatively, communication may be made between the adjacent detector modules by the inter-module communication control function using radio waves such as Near Field Communication (NFC).

Fourth Modification

In the embodiment described above, the HV detection unit 13c, the module control unit 13f, and the HV interruption unit 13g are separately configured in each detector module. Alternatively, the HV detection unit 13c, the module control unit 13f, and the HV interruption unit 13g may be integrally configured.

The first light emitting unit 13d-1 and the second light emitting unit 13d-2 may also serve as the HV detection unit 13c. In this case, the first light emitting unit 13d-1 and the second light emitting unit 13d-2 emit light with a voltage obtained by converting the high voltage of the voltage conversion unit 13b, and are turned off as the HV of the voltage conversion unit 13b is lowered.

The light emitted from the first light emitting unit 13d-1 and the second light emitting unit 13d-2 may be periodic blinking.

The first light emitting unit 13d-1 and the second light emitting unit 13d-2 are configured to be turned off in a case in which an anomaly occurs, but the first light emitting unit 13d-1 and the second light emitting unit 13d-2 may be turned on in a case in which an anomaly occurs.

The HV detection unit 13c does not necessarily measure the voltage of the voltage conversion unit 13b, and may measure a current on the high voltage side of the voltage conversion unit 13b to output the anomaly detection signal based on a measured value.

Fifth Modification

The embodiment described above exemplifies a configuration of implementing the inter-module communication control function and the inter-module block control function among the detector modules M_1 to M_N that are adjacent to each other in the X-axis direction. On the other hand, in a configuration of arranging a plurality of detector modules also in the Y-axis direction, for example, assumed is a case in which an electric discharge may be caused in the Y-axis direction. In such a case, the inter-module communication control function and the inter-module block control function can be implemented among the detector modules M_1 to M_N that are adjacent to each other in the Y-axis direction.

Sixth Modification

In the embodiment described above, the photon counting detector of a direct type of the X-ray CT device is described as an example. However, the example is not limited thereto, and the X-ray detector according to the present embodiment can be applied to any medical image diagnostic apparatus so long as the X-ray detector is a photon counting detector of a direct type having a module structure.

According to at least one of the embodiments described above, a breakdown caused by an electric discharge can be prevented even in a case in which a voltage drop is caused in a certain module in a photon counting detector.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray detector having a plurality of detector modules, the X-ray detector comprising:
   a first detector module;
   a second detector module adjacent to the first detector module among the plurality of detector modules;
   disposed in each detector module of the plurality of detector modules, a corresponding voltage application circuit configured to apply a bias voltage to a plurality of detection elements included in the detector module;
a first transmission circuit configured to transmit a signal based on the bias voltage from the voltage application circuit of the first detector module, the first transmission circuit being disposed in the first detector module; and
a first reception circuit configured to receive the signal transmitted from the first transmission circuit, the first reception circuit being disposed in the second detector module.

2. The X-ray detector according to claim 1, further comprising:
a first control circuit configured to control application of the voltage to the detection elements by the voltage application circuit in the second detector module in a case in which the first reception circuit does not receive the signal, the first control circuit being disposed in the second detector module.

3. The X-ray detector according to claim 2, wherein the first control circuit connects the voltage application circuit in the second detection module to GND, or controls the bias voltage applied from the voltage application circuit in the second detection module to be equal to or smaller than a fixed value.

4. The X-ray detector according to claim 2, further comprising:
a second control circuit configured to transmit an anomaly detection signal to a control circuit of an imaging device equipped with the X-ray detector in a case in which the first transmission circuit does not transmit the signal based on the bias voltage in the first detector module, the second control circuit being disposed in the first detector module.

5. The X-ray detector according to claim 2, wherein the second detector module further comprises a storage circuit configured to store information indicating a presence/absence of the control for application of the bias voltage.

6. The X-ray detector according to claim 1, further comprising:
a second transmission circuit configured to transmit a signal at a time of application of the voltage by the bias voltage application circuit of the second detector module, the second transmission circuit being disposed in the second detector module; and
a second reception circuit configured to receive the signal transmitted from the second transmission circuit, the second reception circuit being disposed in the first detector module.

7. The X-ray detector according to claim 6, wherein
the first transmission circuit and the second transmission circuit transmit the signal by light or by radio waves, and
the first reception circuit and the second reception circuit receive the signal by light or by radio waves.

8. A medical image diagnostic apparatus, comprising an X-ray detector having a plurality of detector modules, wherein the X-ray detector comprises:
a first detector module;
a second detector module adjacent to the first detector module among the plurality of detector modules;
disposed in each detector module of the plurality of detector modules, a corresponding voltage application circuit configured to apply a bias voltage to a plurality of detection elements included in the detector module;
a first transmission circuit configured to transmit a signal based on the bias voltage from the voltage application circuit of the first detector module, the first transmission circuit being disposed in the first detector module;
a first reception circuit configured to receive the signal transmitted from the first transmission circuit, the first reception circuit being disposed in the second detector module; and
a module control circuit configured to transmit an anomaly detection signal to a control circuit configured to control an imaging operation in a case in which the first transmission circuit does not transmit the signal based on the bias voltage.

9. The medical image diagnostic apparatus according to claim 8, further comprising:
a first control circuit configured to control application of the bias voltage to the detection elements by the voltage application circuit in the second detector module in a case in which the first reception circuit does not receive the signal, the first control circuit being disposed in the second detector module.

10. The medical image diagnostic apparatus according to claim 9, wherein the first control circuit connects the voltage application circuit in the second detection module to GND, or controls the bias voltage applied from the voltage application circuit in the second detection module to be equal to or smaller than a fixed value.

11. The medical image diagnostic apparatus according to claim 9, further comprising:
a second control circuit configured to transmit an anomaly detection signal to a control circuit of an imaging device equipped with the X-ray detector in a case in which the first transmission circuit does not transmit the signal based on the bias voltage in the first detector module, the second control circuit being disposed in the first detector module.

12. The medical image diagnostic apparatus according to claim 9, wherein the second detector module further comprises a storage circuit configured to store information indicating a presence/absence of the control for application of the bias voltage.

13. The medical image diagnostic apparatus according to claim 8, further comprising:
a second transmission circuit configured to transmit a signal at a time of application of the bias voltage by the voltage application circuit of the second detector module, the second transmission circuit being disposed in the second detector module; and
a second reception circuit configured to receive the signal transmitted from the second transmission circuit, the second reception circuit being disposed in the first detector module.

14. The medical image diagnostic apparatus according to claim 13, wherein
the first transmission circuit and the second transmission circuit transmit the signal by light or by radio waves, and
the first reception circuit and the second reception circuit receive the signal by light or by radio waves.

15. The X-ray detector according to claim 1, wherein
the first transmission circuit in each detector module is configured to transmit the signal based on the bias voltage from the voltage application circuit in the detector module to the first reception circuit in an adjacent detector module in series; and
the first reception circuit in the adjacent detector module is configured to receive the signal transmitted from the first transmission circuit module in series.

16. The medical image diagnostic apparatus according to claim 13, wherein
- the first transmission circuit in each detector module is configured to transmit the signal based on the bias voltage from the voltage application circuit in the detector module to the first reception circuit in an adjacent detector module in series; and
- the first reception circuit in the adjacent detector module is configured to receive the signal transmitted from the first transmission circuit module in series.

* * * * *